United States Patent [19]

Moore et al.

[11] 4,314,095
[45] Feb. 2, 1982

[54] DEVICE AND METHOD FOR MAKING ELECTRICAL CONTACT

[75] Inventors: Eric R. Moore, Pittsburgh; Marlin S. Heilman, Gibsonia; Philip C. Kinney, Pittsburgh, all of Pa.

[73] Assignee: Mieczyslaw Mirowski, Owings Mills, Md.

[21] Appl. No.: 34,731

[22] Filed: Apr. 30, 1979

[51] Int. Cl.³ .......................... H01R 4/18; A61N 1/36
[52] U.S. Cl. .......................... 174/84 C; 128/419 P; 128/642
[58] Field of Search .................. 174/74 R, 84 R, 84 C, 174/94 R; 339/275 R, 276 R; 128/419 P, 642, 784, 786, 798, 639

[56] References Cited

U.S. PATENT DOCUMENTS 3,124,641  3/1964  Anderson .......................... 174/84 C
3,954,100  5/1976  Sem-Jacobson .................... 128/639

Primary Examiner—Roy N. Envall, Jr.
Attorney, Agent, or Firm—Fleit & Jacobson

[57] ABSTRACT

A specialized clip and method for electrically and mechanically joining a highly-flexible electrical conductor and a fine metallic mesh or screen for use in medical electrodes. The clip is in the form of an inverted U and has a portion of the wire mesh folded thereinto such that upon insertion of the U-shaped clip containing the mesh the clip may be mechanically crimped to bring about intimate contact between the flexible conductors and the mesh. The mesh portion is then welded to the main body of the wire mesh and the wire mesh may then be subsequently used in the manufacture of implantable medical electrodes, for example, defibrillation electrodes.

18 Claims, 6 Drawing Figures

DEVICE AND METHOD FOR MAKING ELECTRICAL CONTACT

BACKGROUND OF THE INVENTION

The recent advances of medicine involving the use of implanted electrical devices has more and more frequently required the use of electrodes and the like, which must have extreme resistance to fractures caused by flexing. Such electrodes must have the combination of high conductivity, high flexibility, biological inertness, as well as being resistant to flex fractures. For example, in the case of a cardiac electrode, it has recently been proposed to use an extremely fine titanium or platinum mesh, which provides very good electrical properties while being able to conform itself to the shape of the heart. Additionally, when using electrodes which are placed directly on the heart, it is a requirement that the electrical conductors, which are connected to the electrodes, also be extremely flexible and resistant to fracture from repeated flexion. This is so because the heart undergoes continuous movement, which cannot be inhibited or interfered with by inflexible wires or the like. Furthermore, any fracture would adversely affect the operation of the conductor. Accordingly, it is proposed to utilize electrical conductors which are especially suited for use with implanted medical-electronic devices. More specifically, such electrical conductors could be formed of stranded wire generally having at least seven strands. The central strand is comprised of a polyester yarn, about which are wound six conductive metallic strands. The conductive strands are in turn comprised of a core of polyester yarn and have a thin silver ribbon wound thereabout. The silver ribbon could have the dimensions of approximately 1 by 13 mils.

Although the use of such highly flexible electrical conductors should be quite satisfactory as far as mechanical stress is concerned, the use of such stranded wire formed of the highly-flexible, but thin, silver ribbons presents a problem in achieving good electrical connections which also have high mechanical strength. This problem is made even more acute when the electrode is formed, not of a solid metallic plate or the like, but of an extremely fine metallic mesh or screen.

Previous attempts at forming a sound electrical connection have been centered around directly welding or silver soldering the flexible electrical conductors to the actual electrode surface. Such joining techniques would be destructive or unstable if applied to a multistranded silver ribbon-conductive mesh crimp joint.

SUMMARY OF THE INVENTION

The present invention is generally related to the field of electrical connectors and, more specifically, to apparatus for forming an electrical connection between a highly flexible wire and an implantable medical electrode having a mesh surface.

In one embodiment, the present invention provides a short, solid metal clip formed in the shape of an inverted U having the ends of the arms thereof rolled over, i.e., having substantially the shape of the Greek letter Omega. A portion of the actual electrode mesh is intended to be inserted into the channel formed by the inventive clip. The highly-flexible electrical conductors are then inserted into the channel and the sides of the clip are deformed or crimped such that the flexible conductors are held in intimate contact with the portion of the actual electrode material.

An embodiment of the present invention employs an additional flared, trumpet-shaped, metallic sleeve or tubing portion which is first slipped over the highly-flexible electrical conductors and then inserted into the inventive clip. The clip is then crimped and the metallic sleeve serves not only to further protect the delicate electrical conductors in the crimping operation but also to provide a preferential corrosion zone, which will be further explained hereinbelow. This trumpet-shaped sleeve may also be formed as a double-ended trumpet-shaped sleever for use where the delicate silver tinsel goes through a sleeve.

One embodiment of the present invention is intended to be used with a very thin, highly-conductive, mesh electrode which may be formed having an extra portion extending from the side, which is intended to be folded back over against the electrode surface and then spot welded to the main electrode. At that time the folded portion may be inserted into the Omega-shaped clip and then the U-shaped channel may have a suitable silver-filled epoxy applied thereto. The flexible electrical conductor is then introduced into the epoxy-filled channel and the arms of the specialized clip are crimped together, so as to mechanically maintain intimate contact between the folded-over portion of the electrode and the flexible electrical conductors. At that time, the part of the extended electrode portion which had not been inserted into the inventive clip may be spot welded to the surface of the electrode proper, thereby providing good mechanical strain relief, as well as excellent electrical contact. Typically, after forming this electrical and mechanical connection, an insulation boot formed of Silastic or other suitable material, which is chemically-inert in the human body, is cast or formed around the electrical connection.

It is, therefore, an object of the present invention to provide apparatus for achieving a good electrical contact, having good mechanical strength, between a highly flexible electrical conductor and an implantable medical electrode.

It is another object of the present invention to provide an electrical connecting clip having a specialized configuration and which may be mechanically deformed to achieve a good electrical joint with high mechanical strength.

It is an additional object of the present invention to provide a method for forming a good electrical joint between a flexible wire and a metallic mesh surface and also to provide a high degree of mechanical strength to the joint.

It is a further object of the present invention to provide a method for making a good electrical connection wherein a portion of an electrode is inserted inside a specialized clip and then a silver-filled epoxy is applied inside the clip prior to insertion of a flexible electrical conductor.

The manner in which these and other objects are accomplished by the present invention, as well as the many attendant advantages thereof, will become more readily apparent when reference is made to the following description, taken in conjunction with the accompanying drawings.

DETAILED DESCRIPTION OF THE DRAWINGS

Figure 1:
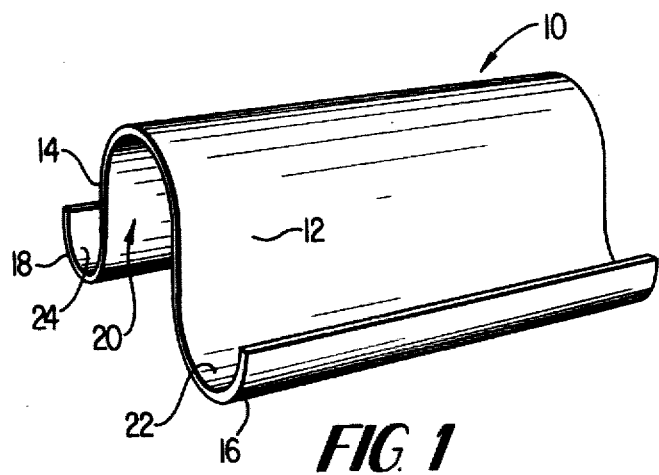
FIG. 1 is a perspective of an embodiment of the present invention.

With reference first to FIG. 1, the general configuration of the inventive electrical clip will be described. As indicated hereinbefore, the clip 10 is formed of a suitable chemically-inert metal, such as stainless steel, titanium, or the like, and is in the form generally of an inverted U. The clip is provided with two arms 12, 14 and at the end of each arm an arcuate shaped portion 16, 18 is formed. The arms 12, 14 form a channel 20, wherein the electrode and the flexible wire are ultimately brought into contact. The clip 10 is intended to be crimped or mechanically deformed by suitable pliers or the like and, in this regard, the points of the pliers or forming tool may be arranged in the channels 22, 24, formed by the arcuate shaped portions 16, 18, respectively.

Figure 2:
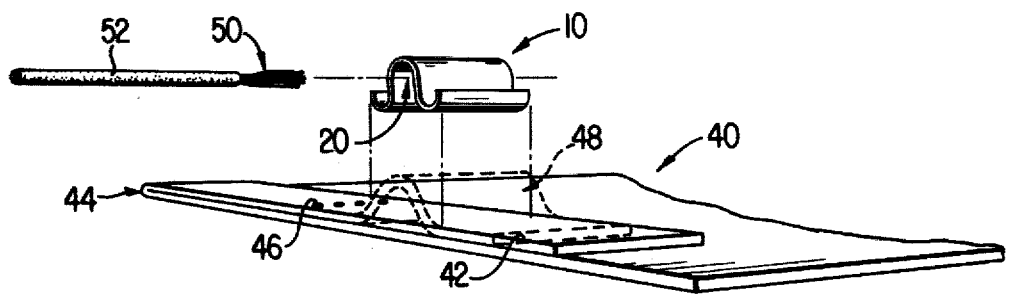
FIG. 2 is an exploded perspective showing an embodiment of the present invention arranged for assembly with a medical electrode.

Referring to FIG. 2, the inventive clip 10 of FIG. 1 is shown in an exploded assembly view in relation to an implantable electrode, a portion of which is shown generally at 40. Although the electrode 40 has been formed of a metallic mesh or screen, it might also be formed of expanded metal, such as platinum or the like, or alternately it may be a perforated metal sheet or a solid metal sheet. The electrode 40 has an additional portion 42, which has a narrow width and is somewhat strip-like. The additional portion 42 is a continuation of the main body 40 of the electrode. The strip-like portion 42 is then folded over along a line, shown generally at 44, and is electrically spot welded to the main portion of the electrode at several locations, shown typically at 46. The strip-like portion 42 is then bent or formed into a ridged configuration, shown by the dashed lines 48, prior to insertion into the channel 20 of the inventive clip 10. During assembly the inventive clip 10 is moved into contact with the strip-like portion 42, and the channel 20 of the clip, which now contains the strip-like portion 42, is filled with a silver-filled epoxy. At that time, the conductors 50 of the flexible wire 52 are laid into the channel 20 containing the strip-like portion 42 and the silver-filled epoxy. The inventive clip 10 is then crimped so as to form a tight mechanical bond between the conductors 50 and the strip-like portion 42. In this way a low-resistance electrical joint is formed.

Figure 3:
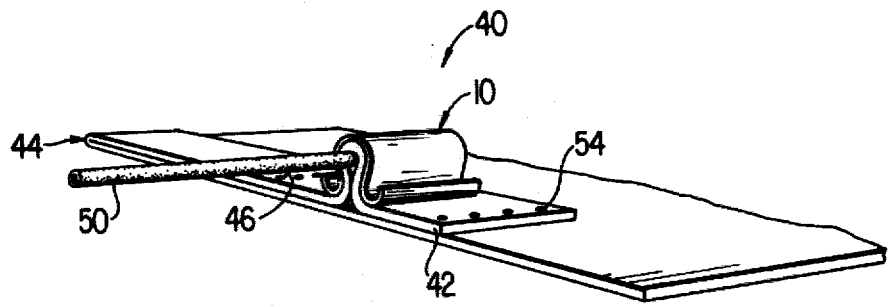
FIG. 3 is a perspective of the present invention assembled with a medical electrode.

In FIG. 3 the inventive clip 10 is shown having been crimped so as to firmly grasp the conductors 50 of the cable 52 and the strip-like portion 42. After such crimping has occurred, the strip-like portion 42 is then placed into contact with the main body portion of the electrode 40 and is also electrically spot welded to the main body at several locations 54, thereby firmly joining the strip-like portion 42 to the main electrode 40.

The electrode 40, having the cable 50 electrically and mechanically attached thereto, is now ready to be electrically insulated by the appropriate material, such as Silastic, for its ultimate use as an implanted electrode.

Figure 4:
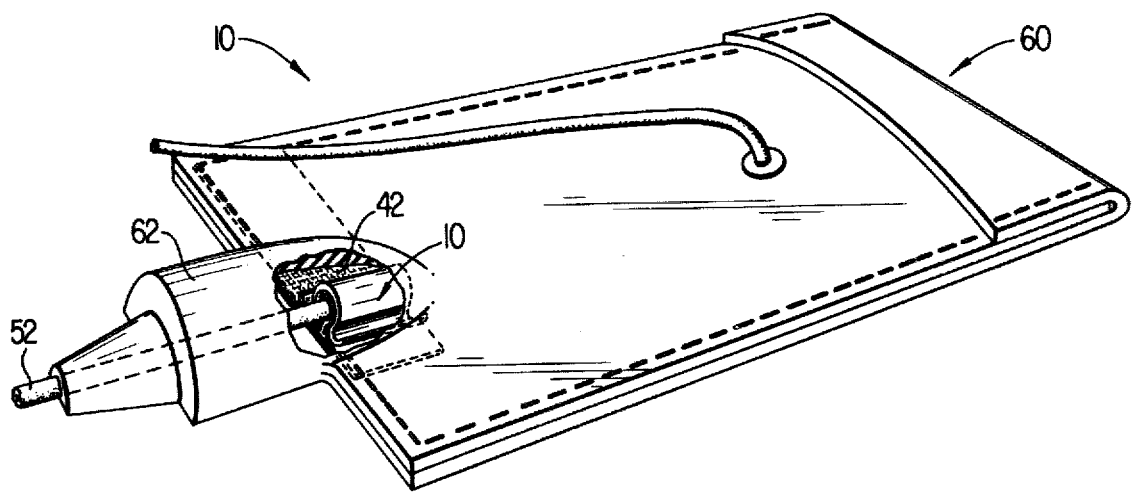
FIG. 4 is a perspective of the bottom surface of an implantable medical electrode assembly, having a portion of the insulation removed therefrom and showing the present invention.

In this regard, reference is made to FIG. 4 which shows an implantable medical electrode 60 having being formed in accordance with the assembly technique shown in FIGS. 2 and 3. The electrical joint is covered with Silastic, or the like, and the electrical joint is shown having a portion of the insulating material cut away. After the electrical connection has been made, a boot 62 formed of Silastic, or other insulating material, is cast or arranged over the electrical connection area. This boot serves to provide both mechanical strain relief and also to prevent any electrical impulses from reaching the patient at locations which are not desired.

Figure 5:
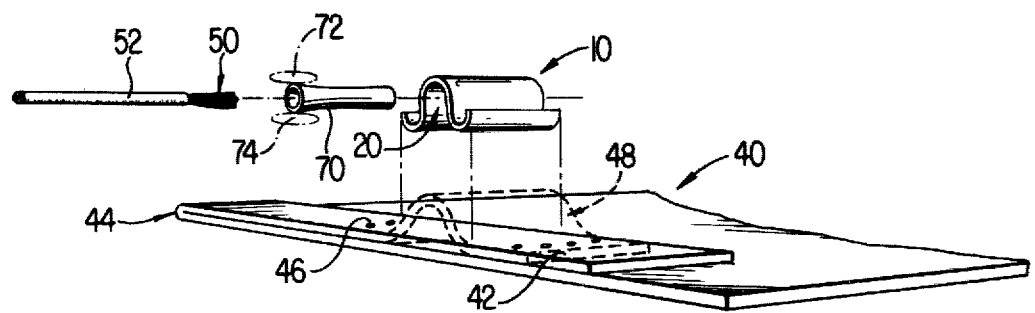
FIG. 5 is an exploded perspective of the present invention showing the use of an additional flared metallic tubing portion.

FIG. 5 is an exploded assembly view similar to FIG. 2, with the further addition of a flared tubing portion 70. The flared tubing 70 should have very thin walls and be formed of an excellent electrical conductor, such as silver. During assembly, the flared tubing 70 is slipped over the conductors 50 of the flexible wire 52. This combination is then inserted into the channel 20 of the inventive clip 10 after the portion of the wire mesh 48 has been inserted therein. In this manner, when forming the compression joint the maximum stress is placed on the sleeve and not on the delicate silver tinsel. Additionally, upon assembly, preferential corrosion zones 72, 74 are provided. The preferential zones of corrosion make the sleeve a sacrificial one, wherein the trumpet portions 72, 74 will corrode before the critical silver tinsel.

Figure 6:
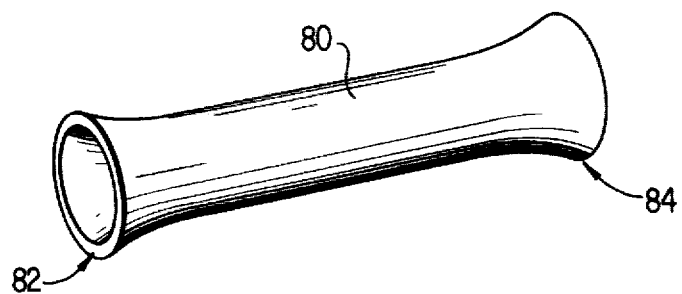
FIG. 6 is a perspective of an inventive double-ended, flared, tubular sleeve for use in connecting silver tinsel wires.

FIG. 6 shows a double-ended trumpet sleeve 80, formed of silver and being similar to sleeve 70 of FIG. 5. This sleeve 80 has the flared ends 82, 84 which serve both to contact the silver tinsel and also to provide the preferential-corrosion zones, thereby making this sleeve 80 also a sacrificial silver sleeve. This sleeve is intended for use where the silver tinsel goes through a fitting, such as the connection point of a spring catheter.

It is, of course, understood that the above-description of the present invention is given by way of example only and is not intended to limit the scope of the present invention, except as defined in the following claims.

What I claim is:

1. Apparatus for use in a discharge electrode adapted for implantation in a patient to effect an electrical discharge into the heart, the combination of:
    silver tinsel wire for electrically connecting said electrode to a power source;
    a deformable electrically-conductive metallic tubular sleeve having inner and outer surfaces and a flared end for receiving said silver tinsel wire, said sleeve for surrounding a portion of said silver tinsel wire, said flared end defining a corrosion zone spaced from said silver tinsel wire; and
    a metallic U-shaped clip, the arms of said clip being arranged in spaced-apart relationship with an end portion of each arm turned arcuately outward, thereby forming a central elongated channel for receiving a portion of the electrode and said sleeve with said portion of said silver tinsel wire therein, whereby upon deforming said clip by moving said arms closer together than in said spaced-apart relationship after said electrode and said sleeve are placed in said channel, a first electrical connection between said silver tinsel wire and said inner surface of said sleeve and a second electrical connection between the electrode and said outer surface of said sleeve are created with said sleeve protecting the silver tinsel wire during deformation of said clip.

2. Device for use in electrically connecting a flexible multifilament silver tinsel wire and a metallic mesh electrode, said device comprising:
   a deformable electrically-conductive metallic tubular sleeve having an inner conductive surface and an outer conductive surface, said sleeve receiving and surrounding a portion of the silver tinsel wire;
   a metallic electrically-conductive U-shaped clip having a pair of arms, said arms being arranged in spaced-apart relationship and having the end portion of each arm formed in an outwardly turning arcuate shape, said arms forming a central elongated channel for receiving a portion of the metallic mesh electrode and said sleeve with the silver tinsel wire therein, whereby upon deforming said clip by moving said arms closer together than in said spaced-apart relationship after the mesh electrode and said sleeve are placed in said channel, an electrical connection between the mesh electrode and the outer surface of said sleeve and an electrical connection between the silver tinsel wire and said inner surface of said sleeve are created with said sleeve protecting the silver tinsel wire from stress during deformation of said clip.

3. The device of claim 2 wherein said inverted U-shaped clip is less than 10 mm in length.

4. The device of claim 2 wherein said inverted U-shaped clip is formed of titanium.

5. The device of claim 2, wherein said tubular sleeve further comprises a flared end, which defines a corrosion zone spaced from the silver tinsel wire.

6. Apparatus for use in a discharge electrode adapted for implantation in a patient to effect an electrical discharge into the heart, said apparatus comprising:
   silver tinsel wire for electrically connecting said electrode to a power source;
   an elongated conductive strip having inner and outer surfaces;
   first securing means for electrically securing one end of said inner surface to said electrode;
   second securing means for electrically securing the other end of said inner surface to said electrode; and
   connecting means for electrically connecting a portion of said silver tinsel wire with the portion of said inner surface of said strip intermediate said first and second securing means.

7. The apparatus of claim 6, wherein said connecting means comprises a deformable electrically-conductive metallic tubular sleeve having inner and outer surfaces, said sleeve receiving and surrounding a portion of said silver tinsel wire, said inner surface of said sleeve electrically contacting said silver tinsel wire, and said outer surface of said sleeve electrically contacting said inner surface of said strip.

8. The apparatus of claim 7, wherein said connecting means further comprises a metallic U-shaped clip having a pair of arms, said arms being arranged in a spaced-apart relationship and having the end portion of each arm formed in an outwardly turning arcuate shape, said arms forming a central elongated channel disposed about the portion of the outer surface of said strip intermediate said first and second securing means, said clip being deformed by having said arms moved closer together than in said spaced-apart relationship so as to mechanically connect said silver tinsel wire to said strip.

9. The apparatus of claim 8, further comprising insulating means for insulating said wire, said strip, said first and second securing means and said connecting means from the internal biological environment of said patient.

10. The apparatus of claim 9, wherein said insulating means comprises an encapsulating boot made from Silastic.

11. The apparatus of claim 1, wherein said tubular sleeve further comprises a second flared end defining a second corrosion zone.

12. A connector for use in electrically connecting a flexible multifilament silver tinsel wire lead and a flexible metallic mesh electrode adapted to be implanted and to deliver electrical energy directly to the heart of a patient, the connector comprising:
   a deformable electrically-conductive metallic tubular sleeve having an inner conductive surface and an outer conductive surface, said sleeve receiving and surrounding a portion of said silver tinsel wire lead;
   deformable clip means for mechanically and electrically connecting a portion of said metallic mesh electrode directly to the outer conductive surface of said metallic tubular sleeve;
   wherein once said metallic tubular sleeve, said portion of said silver tinsel wire lead, and said portion of said metallic mesh electrode are so positioned, they are crimped and permanently held together by said clip means; and
   insulating means for mechanically and electrically insulating the connection so formed from the internal body fluids of the patient.

13. The connector of claim 12, wherein said deformable clip means comprises a metallic U-shaped clip, the arms of said clip being arranged in spaced-apart relationship with an end portion of each arm turned arcuately outward, thereby forming a central elongated channel for receiving said portion of said mesh electrode and said tubular sleeve with said portion of said wire lead therein.

14. The connector of claim 12, wherein said tubular sleeve further comprises a flared end, which defines a corrosion zone spaced from said wire lead.

15. The connector of claim 12, wherein said insulating means comprises an encapsulating boot made from Silastic.

16. The apparatus of claim 6, wherein said connecting means comprises an electrically-conductive epoxy, said epoxy surrounding a portion of said silver tinsel wire and electrically contacting said conductive strip.

17. The apparatus of claim 6, wherein said connecting means comprises an electrically-conductive epoxy, said epoxy being disposed on the inner surface of said strip intermediate said first and securing means.

18. Device for use in electrically connecting a flexible multifilament silver tinsel wire and a planar metallic mesh electrode, said device comprising:
   a metallic electrically-conductive U-shaped clip having a pair of arms, said arms being arranged in spaced-apart relationship and having the end portion of each arm formed in an outwardly turning arcuate shape, said arms forming a central elongated channel defining an inner surface for receiving a portion of the planar metallic mesh electrode and a portion of said silver tinsel wire therein, one surface of the electrode contacting said inner surface of said clip with the other surface of the electrode being proximate said portion of said wire; and an electrically-conductive epoxy disposed about at least one of the portion of said silver tinsel wire and the other surface of the electrode, whereby, upon deforming said clip by moving said arms closer together than in said spaced-apart relationship after said mesh electrode, said silver tinsel wire and said epoxy are placed in said channel, an electrical connection between the other surface of said mesh electrode and the silver tinsel wire is created with said epoxy enhancing said electrical connection.

* * * * *